United States Patent [19]
Fankhauser

[11] Patent Number: 4,999,379
[45] Date of Patent: Mar. 12, 1991

[54] NOVEL PHARMACEUTICAL COMPOSITIONS FOR TOPICAL APPLICATION WITH SYSTEMIC ACTION

[75] Inventor: Peter Fankhauser, Ettingen, Switzerland

[73] Assignee: Ciba-Geigy Corporation, Ardsley, N.Y.

[21] Appl. No.: 348,325

[22] Filed: May 5, 1989

Related U.S. Application Data

[63] Continuation of Ser. No. 63,889, Jun. 19, 1987, abandoned.

[30] Foreign Application Priority Data

Jun. 27, 1986 [CH] Switzerland ............... 2597/86

[51] Int. Cl.$^5$ .......................................... A61K 31/195
[52] U.S. Cl. ................... 514/567; 514/825; 514/916
[58] Field of Search ............... 514/825, 567, 916

[56] References Cited

U.S. PATENT DOCUMENTS

| 3,558,690 | 1/1971 | Sallmann et al. | 514/825 |
| 3,989,816 | 11/1976 | Rajadhyaksha | 424/60 |
| 4,405,616 | 9/1983 | Rajadhyaksha | 514/788 |
| 4,873,081 | 10/1989 | Ogisco | 514/974 |

FOREIGN PATENT DOCUMENTS 0156080  2/1985  Japan .

Primary Examiner—Stanley J. Friedman
Assistant Examiner—Zohreh A. Fay
Attorney, Agent, or Firm—JoAnn Villamizar

[57] ABSTRACT

There are disclosed novel pharmaceutical compositions which comprise diclofenac or a salt thereof, a penetration agent such as 1-n-dodecylazacycloheptan-2-one or dimethyllauroylamide and, as vehicle, a mineral oil. These compositions have excellent skin penetration properties and can therefore be used in transdermal therapeutic systems (TTS) as drug reservoir.

3 Claims, No Drawings

NOVEL PHARMACEUTICAL COMPOSITIONS FOR TOPICAL APPLICATION WITH SYSTEMIC ACTION

This is a continuation of application Ser. No. 063,889 filed on June 19, 1987 now abandoned.

Topical application of drugs is often indicated whenever the dosage form for oral or some other kind of parenteral administration leads to lack of tolerance, risks, or side-effects. Thus topical application to the skin is preferred if the drug is to act systemically, by-passing the gastrointestinal tract.

Pharmaceutical compositions for topical application on the basis of an oil-in-water emulsion containing diethylammonium-2-(2,6-dichloroanilino)phenyl acetate as active ingredient are disclosed in DE-A 3 336 047.

It is the object of the present invention to provide a pharmaceutical composition for topical application containing diclofenac or a salt thereof, which composition is distinguished by enhanced penetration properties and resorption.

This object is achieved with the pharmaceutical composition of this invention, which comprises the following components:

(a) diclofenac or a pharmaceutically acceptable salt thereof, (b) a compound of formula

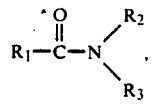 (I)

wherein $R_1$ is $C_9$–$C_{19}$alkyl and $R_2$ and $R_3$ are $C_1$–$C_4$alkyl, or wherein $R_1$ is attached to one of the substituents $R_2$ or $R_3$ and, together with said substituent, is $C_5$–$C_7$alkylene, and the other substituent $R_2$ or $R_3$ is $C_{10}$–$C_{20}$alkyl, which compound enhances the permeability of component (a), and, optionally, (c) a paraffin which is suitable for topical application and is liquid at body temperature, and/or (d) further excipients suitable for percutaneous delivery.

A pharmaceutically acceptable salt of diclofenac, o-(2,6-dichloroanilino)phenylacetic acid, is in particular an alkali metal salt, e.g. the sodium or potassium salt, an acid addition salt with an amine, e.g. a mono-, di- or tri($C_1$–$C_4$alkyl)amine, such as diethylamine or triethylamine, a hydroxy($C_1$–$C_4$)alkylamine such as ethanolamine, a (hydroxy-$C_2$–$C_4$alkyl)-di($C_1$–$C_4$alkyl)amine such as dimethylethanolamine, or a quaternary ammonium salt, e.g. the tetramethylammonium salt or chlorine salt of diclofenac.

The compound of formula I has permeability enhancing properties in the pharmaceutical composition of this invention and is able to increase the rate of flux of diclofenac or salt thereof through the skin per unit of time.

In a compound of formula I, $R_1$ is preferably straight chain $C_9$–$C_{19}$alkyl, e.g. n-nonyl, n-undecyl, n-tridecyl, n-pentadecyl, n-heptadecyl or n-nonadecyl.

If $R_1$ is $C_9$–$C_{19}$alkyl, then $R_2$ and $R_3$ are preferably methyl.

$R_1$ and $R_2$ or $R_1$ and $R_3$ may also be attached to each other and together form an azacycloalkanone heterocycle. In this case, $R_1$ and $R_2$ or $R_1$ and $R_3$ together are $C_5$–$C_7$alkylene, preferably straight chain $C_5$–$C_7$alkylene, e.g. n-hexylene or n-heptylene, preferably n-pentylene; and the substituent $R_2$ or $R_3$ which is not attached to $R_1$ is preferably straight chain $C_{10}$–$C_{20}$alkyl containing an even number of carbon atoms, e.g. n-decyl, n-dodecyl, n-tetradecyl, n-hexadecyl, n-octadecyl or n-eicosyl.

In preferred compounds of formula I, $R_1$ is n-undecyl and $R_2$ and $R_3$ are methyl (N, N-dimethyllauroylamide), or $R_1$ and $R_2$ or $R_1$ and $R_3$ are attached to each other together are n-pentylene, and form the azacycloheptan-2-one heterocycle which is substituted at the nitrogen by $R_3$ or $R_2$ defined as $C_{10}$–$C_{20}$alkyl, e.g. n-dodecyl, and is e.g. 1-n-dodecylazacycloheptan-2-one (Azone®, ex Nelson Corp.).

Paraffins which are suitable for topical application and liquid at body temperature are in particular purified clear, oily, tasteless and odourless mixtures of saturated aliphatic or cycloaliphatic hydrocarbons, e.g. low viscosity or viscous paraffin or VASELINE® petroleum jelly (Cheseborough Manuf. Co.).

The preferred paraffin is viscous paraffin with a boiling point above 300° C. and having the density and viscosity values indicated in standard pharmacopeias. e.g. DAB, OeAB, Helv., USP or CF, e.g. 0.865–0.890 and $\geq 120 \pm 20$ cP (DAB 7, OeAB 9), 0.845–0.905 and $\geq 38.1$ cSt (37.8° C.-USP XIX), 0.865–0.895 and $\geq 40$ cP (Helv. VI) or 0.860–0.885 and $\geq 37$ cSt (0° C.-CF 65), as well as having the purity standards and maximum limits for impurities prescribed in the above pharmacopeias.

Preferred excipients for percutaneous delivery are those which are suitable for the preparation of creams, ointments, gels, pastes or foams containing c. 0.5 to 5% of drug and, in particular, for the preparation of transdermal therapeutic systems.

Creams are water-in-oil emulsions. For the oily phase it is preferred to use fatty alcohols, e.g. lauryl, cetyl or stearyl alcohol, fatty acids, e.g. palmitic or stearic acid, liquid or solid waxes, e.g. isopropyl myristate, natural or partially synthetic fat, e.g. cocosyl triglyceride, hardened oils, e.g. hydrogenated ground nut oil or castor oil, or fatty acid partial esters of glycerol, e.g. glycerol monostearate or glycerol distearate. Suitable emulsifiers are surface-active compounds with mainly hydrophilic properties, e.g. nonionic surfactants, e.g. fatty acid esters of polyalcohols or adducts thereof with ethylene oxide such as polyglycerol fatty acid esters or polyoxyethylene sorbitan fatty acid esters (Tween®, ICI), and also polyoxyethylene fatty alcohol ethers or fatty acid esters, or anionic surfactants such as alkali metal salts of fatty alcohol sulfates, e.g. sodium lauryl sulfate, sodium acetyl sulfate or sodium stearyl sulfate, which are normally used in the presence of the fatty alcohols, e.g. cetyl alcohol or stearyl alcohol. To the aqueous phase are added e.g. humectants, e.g. polyalcohols such as glycerol, sorbitol, propylene glycol and/or polyethylene glycols, and also preservatives, perfumes and the like.

Ointments are water-in-oil emulsions. Component (c) is used as oily phase, preferably low viscosity paraffin to which preferably a fatty alcohol or an ester thereof, e.g. cetyl alcohol, or a wax alcohol, or wool wax is added to enhance the hydrophilic properties. Suitable emulsifiers are lipophilic substances such as sorbitan fatty acid esters (Span®, ex Atlas), e.g. sorbitan oleate and/or sorbitan isostearate. Additives for the aqueous phase include humectants such as polyalcohols, e.g. glycerol, propylene glycol, sorbitol and/or polyethylene glycol, as well as preservatives, perfumes and the like.

Ointments may also be anhydrous and contain, as base, component (c), in particular low viscosity paraffin, and also the cited natural or partially synthetic fats, e.g. cocosyl triglyceride, hardened oils, e.g. hydrogenated ground nut oil or castor oil, fatty acid partial esters of glycerol, e.g. glycerol monostearate and glycerol distearate, silicones e.g. polydimethylsiloxanes such as hexamethyl disiloxane or octamethyltrisiloxane, as well as e.g. the fatty alcohols, for improving the hydrophilic properties mentioned in connection with the water-containing ointments, and emulsifiers and/or other additives.

In the case of gels, a distinction is made between aqueous gels, anhydrous gels or gels of low water content which consist of swellable, gel-forming material. Transparent hydrogels based on inorganic or organic macromolecules are particularly suitable. Macromolecular inorganic components with gel-forming properties are mainly water-containing or water-absorbing silicates such as aluminium silicates, e.g. bentonite, magnesium/aluminium silicates, e.g. Veegum ® (Vanderbilt Exp. Corp.) or colloidal silica, e.g. Aerosil ® (Degussa). Typical examples of macromolecular organic components are natural, semi-synthetic or synthetic polymers. Natural and semi-synthetic polymers are derived e.g. from polysaccharides containing different carbohydrate components, e.g. cellulose, starch, tragacanth, gum arabic, agar-agar, gelatin, alginic acid and the salts thereof, e.g. sodium alginate and derivatives thereof, lower alkyl cellulose, e.g. methyl cellulose or ethyl cellulose, carboxy-lower alkyl cellulose or hydroxy-lower alkyl cellulose, e.g. carboxymethylcellulose or hydroxypropyl cellulose. The components of synthetic, gel-forming polymers are e.g. unsaturated substituted aliphatic compounds such as vinyl alcohol, vinyl pyrrolidone, acrylic acid or methacrylic acid. Examples of such polymers are derivatives of polyvinyl alcohol, e.g. polyviol, polyvinyl pyrrolidones such as Kollidon ® (BASF) or Polyplasdon ® (General Aniline), polyacrylates and polymethacrylates such as Rohagit S ® (Rohm and Haas). Customary additives such as preservatives or perfumes can be added to the gels.

Pastes are creams or ointments containing the above mentioned constituents and secretion-absorbing powder components such as metallic oxides, e.g. titanium dioxide or zinc oxide, and also talcum and/or aluminium silicates which serve to bind moisture or secretions.

Foams are applied e.g. from pressurised containers and are liquid oil-in-water emulsions in aerosol form for which halogenated or non-halogenated hydrocarbons such as chlorofluoro-lower alkanes, e.g dichlorodifluoromethane or dichlorotetrafluoroethane or alkanes, e.g. propane or butane, are used as propellants. Fatty alcohols, e.g. cetyl alcohol, fatty acid esters, e.g. isopropyl myristate, and/or other waxes, are used as the oily phase. Suitable emulsifiers are e.g. mixtures of emulsifiers having mainly hydrophilic properties, for example polyoxyethylene sorbitan fatty acid esters (Tween ®), with emulsifiers having mainly lipophilic properties, e.g. sorbitan fatty acid esters (Span ®). Foams also contain conventional additives such as preservatives and the like.

Transdermal therapeutic systems (TTS) are preferred to such topical agents for percutaneous delivery, as such systems permit the continuous release of active ingredient through the skin over a prolonged period of time ranging from about 24 hours to one week, in contrast to gels or ointments which have to be applied repeatedly during the day. With the aid of transdermal therapeutic systems it is possible to administer constant amounts of drug per unit of time and thus to achieve a uniform systemic action.

Suitable transdermal therapeutic systems which may be applied are for example those disclosed in U.S. Pat. Nos. 3,598,122, 3,598,123, 3,797,494 and 4,064,084, preferably the systems disclosed in DE-A 26 04 718 and in U.S. Pat. Nos. 4,031,984 and 4,262,003, or described by H. Asche in Schweiz. Rundschau Med. (Praxis) 74, No. 11, 257–260 (1985), e.g. matrix or monolith systems or membrane-controlled systems. In this connection it must be emphasised that such application is not limited to the transdermal therapeutic systems disclosed and described in the aforementioned publications. The preferred transdermal therapeutic system disclosed in DE-A 26 04 718 is a system in the form of a patch that releases the drug, e.g. diclofenac sodium, transdermally so that side-effects are avoided, in an initial dose of c. 10 to 200 $\mu g/cm^2$ of skin and then at a rate of c. 0.3 to 5 $\mu g/h$, such that the drug concentration in the plasma remains approximately constant.

In membrane-controlled systems the patch can consist of multi-layer laminates which form the following layers viewed from the application surface:

(a) a protective backing layer; a gel-like mineral oil/polymeric hydrocarbon drug reservoir (b) which contains the flux enhancer and which provides the source of constant drug release; a membrane (c) which partly controls the constant rate of drug release; and (d) a gel-like mineral oil/polymer hydrocarbon layer which contains the drug and which acts as source of the initial dose; as well as further adhesive with which the patch is affixed to the skin after removal of a protective peel strip.

Polymeric hydrocarbons are used in the reservoirs of the above described transdermal therapeutic systems, e.g. polymers containing aliphatic, cycloaliphatic-aliphatic or aliphatic-aromatic molecules, e.g. polypropylene, polybutylene, polybutylethylene, polypropylethylene or polystyrene.

The gel-like mineral oil/polymeric hydrocarbon drug reservoir (b) contains the drug, e.g. Voltaren ®, partly dissolved and partly undissolved, homogeneously dispersed in a gel-like mixture consisting of mineral oil having a viscosity of about 10 to 100 cP at 25° C., a polymeric hydrocarbon, e.g. polyisobutylene, and the flux enhancer, e.g. 1-n-dodecylazacycloheptan-2-one. The mixture of mineral oil and polymeric hydrocarbon also acts as adhesive and holds the patch together. The mineral oil is further used as vehicle for the drug, which has only limited solubility in mineral oil (c. 2 mg/ml). The maximum concentration of drug in the reservoir layer are chosen such that the mineral oil is substantially saturated with the drug during the entire release period of the patch.

The next layer of the multi-layered laminate is a semipermeable layer (c), e.g. a microporous membrane, the pores of which are filled with the above vehicle and which controls the rate at which the drug is released to the skin. The flux of drug through the semipermeable layer and the contact surface area of the membrane must be chosen such that the drug is released to the skin from the reservoir layer at substantially constant rate in the range from c. 0.3 to 5 μg/h. The semipermeable membrane is made from polymeric materials through which the drug can diffuse. Polymers suitable for making such membranes are described in the publications previously referred to, e.g. polypropylene, polyacrylates, polyvinyl chloride, polyester, siliconated polyester laminates, cellulose acetate, cellulose nitrate, polyacrylonitrate, copolymers of ethylene with other monomers, e.g. vinyl acetate, or organopolysiloxane rubber.

The adhesives layer (d) of the laminate is composed substantially of the same materials as layer (b) described above, contains the drug, e.g. diclofenac sodium, and releases an initial dose of the drug when the system is applied to the patient. With the aid of the strongly adhesive layer (d), consisting e.g. of polyisobutylene adhesive material, the patch is affixed to the skin after a protective peel strip, e.g. aluminium foil, has been removed.

The present invention preferably relates to a pharmaceutical composition comprising (a) a pharmaceutically acceptable salt of diclofenac,
(b) a compound of formula I, wherein $R_1$ is n-undecyl and $R_2$ and $R_3$ are methyl (N,N-dimethyllauroylamide), or wherein $R_1$ is attached to one of the substituents $R_2$ and $R_3$ and together with said substituent is n-pentylene, and the nitrogen is substituted by $R_3$ or $R_2$ defined as n-dodecyl (1-n-dodecylazacycloheptan-2-one),
(c) viscous paraffin suitable for topical application, and, optionally,
(d) further excipients suitable for percutaneous delivery.

Most preferably, the invention relates to a pharmaceutical composition comprising (a) the sodium, potassium or diethylammonium salt of diclofenac,
(b) N,N-dimethyllauroylamide or 1-n-dodecylazacycloheptan-2-one,
(c) a viscous mineral oil suitable for topical application, and, optionally,
(d) further excipients suitable for percutaneous delivery.

The pharmaceutical compositions of this invention can be used as formulations for topical application, in particular for transdermal therapeutic systems for the treatment of painful conditions, inflammatory conditions and/or rheumatic diseases in warm-blooded species (humans and animals). They can be applied in daily doses of c. 25-200 mg of drug by means of transdermal therapeutic systems.

The invention also relates to a process for the preparation of said pharmaceutical compositions, which comprises mixing components (a), (b) and optionally (c) and/or (d) in the intended amounts and further processing the mixture so obtained to topical formulations, e.g. creams, ointments, gels, pastes or foams or, in particular, to transdermal therapeutic systems.

The invention further relates to a process for enhancing the permeability of diclofenac or a pharmaceutically acceptable salt thereof in topical formulations, which process comprises the use of a compound of formula

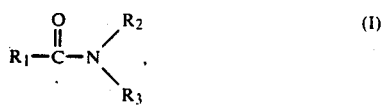

wherein $R_1$ is $C_9$-$C_{19}$alkyl and $R_2$ and $R_3$ are $C_1$-$C_4$alkyl, or wherein $R_1$ is attached to one of the substituents $R_2$ or $R_3$ and, together with said substituent, is $C_5$-$C_7$alkylene, and the other substituent $R_2$ or $R_3$ is $C_{10}$-$C_{20}$alkyl, and, optionally, of a liquid paraffin suitable for topical application and/or further excipients suitable for percutaneous delivery as base for topical formulations containing diclofenac or a pharmaceutically acceptable salt thereof.

Diclofenac and the salts thereof are known (q.v. Merck Index 1983, N. 3066).

Compounds of formula I are known. The use of compounds of formula I, wherein $R_1$ is $C_9$-$C_{19}$alkyl and $R_2$ and $R_3$ are $C_1$-$C_4$alkyl, as penetration agents for achieving a systemic action is known (q.v. U.S. Pat. No. 4,031,894).

The use of compounds of formula I, wherein $R_1$ is attached to one of the substituents $R_2$ or $R_3$ and the other substituent $R_2$ or $R_3$ is $C_{10}$-$C_{20}$alkyl, as penetration agents for topical application, is disclosed in U.S. Pat. No. 3,989,816.

The use of these compounds, especially of 1-dodecylazacycloheptan-2-one, as penetration agents for achieving a systemic action of drugs for topical application, is disclosed in U.S. Pat. No. 4,405,616.

The invention is illustrated by the following Examples.

EXAMPLE 1: ASSAY

1. Materials
1.1. diclofenac sodium (puriss.)
1.2. 1-n-dodecylazacycloheptan-2-one
1.3. N,N-dimethyllauroylamide
1.4. mineral oil (puriss.)

2. Procedure

A piece of pig epidermis measuring c. 3×3 cm was put into a diffusion cell in accordance with the method described by T. J. Franz, J. Invest. Dermatol. 64, 190-195 (1975). The lower acceptor compartment was filled with an isotonic buffer solution of pH 7.4, while the upper donor compartment was filled respectively with (a) a supersaturated solution or suspension (c. 5%) of diclofenac sodium in mineral oil (vehicle),
(b) a supersaturated solution or suspension of diclofenac sodium in the vehicle with the addition of the flux enhancer 1-n-dodecylazacycloheptan-2-one,
(c) a supersaturated solution or suspension of diclofenac sodium in the vehicle with the addition of the flux enhancer, dimethyllauroylamide.

The permeabilities were measured for each sample over a period of 24 hours after 3, 6 and 24 hours respectively. The concentration of diclofenac sodium in the acceptor compartment of the diffusion cell was determined by HPLC. The amount of diclofenac permeated through the epidermis from the beginning of the test per cm² (cumulative permeation) as well as the flux of diclofenac over the elapsed interval of time per cm² and hour were computed from the concentrations. The following values were obtained:

TABLE

| | | Concentr of flux enhancer [% by weight] | cumulative permeation 0-24 h [μg/cm²] | Flux [μg/cm² · h] | |
|---|---|---|---|---|---|
| | | | | 0-3 h | >24 h |
| (a) | vehicle + diclofenac sodium | — | 36 | 2.5 | 1.4 |
| (b) | 1-n-dodecylaza-cycloheptan-2-one | 5 | 240 | 20 | 5 |

TABLE-continued

|     |                          | Concentr of flux enhancer [% by weight] | cumulative permeation 0-24 h [μg/cm$^2$] | Flux [μg/cm$^2 \cdot$ h] | |
|-----|--------------------------|-----|-------|------|-----|
|     |                          |     |       | 0-3 h | >24 h |
|     | + vehicle                |     |       |       |     |
|     | + diclofenac sodium      | 20  | 11300 | 19    | 610 |
| (c) | dimethyllauroyl-amide    | 5   | 2800  | 43    | 140 |
|     | + vehicle                |     |       |       |     |
|     | + diclofenac sodium      | 20  | 7100  | 27    | 360 |

EXAMPLE 2: TRANSDERMAL SYSTEM WITH POROUS RESERVOIR FILLED WITH LIQUID

A circular piece of sintered polypropylene, 1 mm thick and 3.6 mm in diameter, and having an average pore size of 5 μm and a relative pore volume of 20%, is affixed to the centre of a polyester sheet (Mylar®) coated with medicinal silicone adhesive (ex Dow Corning) and having a thickness of 20 μm and a diameter of 5.5 cm. In a vacuum cabinet, 200 mg of the following mixture are applied and air-blasted into the porous sheet:

4 g of diclofenac sodium
16 g of 1-n-dodecylazacycloheptan-2-one
80 g of low viscosity paraffin oil
0.1 g of Tween® 80

To prepare the mixture, the diclofenac sodium is ground in a glass bead mill (Dynomill®) to a particle size of less than 1 μm.

EXAMPLE 3: TRANSDERMAL SYSTEM WITH LIQUID FILLED SACHET RESERVOIR

A 10 cm$^2$ sachet is prepared from polyester/polyethylene composite film and, as backing film, porous polypropylene (Celanese®) as control membrane by heat sealing along the circumference. The sachet is filled with 250 mg of the mixture of Example 2 by puncturing it at the edge with an injection syringe and the puncture is heat sealed. The system containing the mixture is applied to the skin by means of a medicinal plaster.

EXAMPLE 4: TRANSDERMAL SYSTEM WITH MONOLITH RESERVOIR 25 g of diclofenac sodium are suspended in 100 g of 1-n-dodecylazacycloheptan-2-one and the suspension is ground in a glass bead mill to a particle size of less than 1 μm. This suspension is mixed in a heated kneader at 80° C. with 100 g of polyisobutylene with a molecular weight of 5,000,000 and 225 g of polyisobutylene with a molecular weight of 30,000. The mixture is pressed to sheets 1 mm thick which are covered on one side with 20 μm polyester backing layer and on the other with 20 μm siliconised polyester to be removed before use. Transdermal systems measuring 10 cm$^2$ are cut from the laminates.

EXAMPLE 5: TRANSDERMAL SYSTEM WITH LAMINATED RESERVOIR AND CONTROL MEMBRANE 25 g of diclofenac sodium are suspended in 100 g of dimethyllauroylamide and, as in Example 4, processed with polyisobutylene to a plastic material. Sheets 1 mm and 0.1 mm thick are pressed separately from this material. Porous polypropylene sheeting is impregnated with dimethyllauroylamide and the following layers are laminated: a 20 μm polyester sheet as protective film, a 1 mm sheet as reservoir, an impregnated polypropylene sheet as control membrane, a 0.1 mm sheet as contact adhesive surface with initial dose, and a 20 μm siliconised polyester sheeting as peel strip. Transdermal systems measuring 10-40 cm$^2$ are cut from this laminate.

EXAMPLE 6: ASSAY

Three flat teflon sachets measuring 2.5 cm$^2$ with sealing edge are each affixed to the intact skin of the thorax (total area: 7.5 cm$^2$) of 2 test persons. Each sachet is filled with a formulation comprising 10 mg of diclofenac sodium, 10 mg of 1-n-dodecylazacycloheptan-2-one and 30 mg of silicone oil (total of 30 mg of diclofenac sodium), and is left for 24 hours at its application site. Urine is collected at intervals of 0-5, 5-10, 10-24 and 24-48 hours and analysed for excreted drug.

An average flux of diclofenac sodium of 0.35 μg/cm$^2$19 24 h is computed from the excretion.

What is claimed is:

1. A transdermal therapeutic system containing a pharmaceutical composition for systemic administration of diclofenac consisting essentially of
   (a) an antirheumatically and antiphlogistically effective amount of diclofenac or a pharmaceutically acceptable salt thereof,
   (b) N,N-dimethyllauroylamide or 1-n-dodecylazacycloheptan-2-one, in a concentration which enhances the skin permeability of component (a), and
   (c) further excipients suitable for percutaneous delivery.

2. A transdermal therapeutic system containing a pharmaceutical composition for systemic administration of diclofenac consisting essentially of
   (a) an antirheumatically and antiphlogistically effective amount of diclofenac or a pharmaceutically acceptable salt thereof,
   (b) N,N-dimethyllauroylamide or 1-n-dodecylazacycloheptan-2-one, in a concentration which enhances the skin permeability of component (a),
   (c) further excipients suitable for percutaneous delivery, and
   (d) a paraffin which is suitable for topical application and is liquid at body temperature.

3. A transdermal therapeutic system containing a pharmaceutical composition according to claim 1 consisting essentially of
   (a) an antirheumatically and antiphlogistically effective amount of sodium, potassium or diethylammonium salt of diclofenac,
   (b) N,N-dimethyllauroylamide or 1-n-dodecylazacycloheptan-2-one, and
   (c) further excipients suitable for percutaneous delivery.

* * * * *